United States Patent [19]

Swanson, Jr.

[11] Patent Number: 4,924,095

[45] Date of Patent: May 8, 1990

[54] REMOTE GAS ANALYZER FOR MOTOR VEHICLE EXHAUST EMISSIONS SURVEILLANCE

[75] Inventor: Caleb V. Swanson, Jr., Orange, Calif.

[73] Assignee: West Lodge Research, Orange, Calif.

[21] Appl. No.: 275,391

[22] Filed: Nov. 23, 1988

Related U.S. Application Data

[63] Continuation-in-part of Ser. No. 57,293, Jun. 2, 1987.

[51] Int. Cl.⁵ ............................................. G01J 1/00
[52] U.S. Cl. .............................. 250/338.5; 250/338.1
[58] Field of Search ................. 250/338.5, 338.1, 340, 250/341, 349, 345; 356/438; 73/116

[56] References Cited

U.S. PATENT DOCUMENTS

| | | |
|---|---|---|
| 3,593,023 | 7/1971 | Dodson . |
| 3,603,155 | 5/1971 | Morris . |
| 3,630,072 | 12/1971 | Traver . |
| 3,677,652 | 7/1972 | Little . |
| 3,917,454 | 11/1975 | Clark . |
| 3,998,095 | 12/1976 | Tinkham et al. . |
| 4,031,747 | 6/1977 | Blanke . |
| 4,141,241 | 2/1979 | Collin . |
| 4,147,513 | 4/1979 | Bienkowski et al. . |
| 4,160,373 | 7/1979 | Fastaia et al. . |
| 4,204,121 | 5/1980 | Milly . |
| 4,257,258 | 3/1981 | Bovenlander . |
| 4,328,546 | 5/1982 | Kreft et al. . |
| 4,348,732 | 9/1982 | Kreft . |
| 4,361,027 | 11/1982 | Schmitt . |
| 4,372,155 | 2/1983 | Butler et al. . |
| 4,441,359 | 4/1984 | Ezoe . |
| 4,632,563 | 12/1986 | Lord . |
| 4,684,805 | 8/1987 | Shu-ti Lee et al. . |
| 4,719,360 | 1/1988 | Kontani et al. . |

FOREIGN PATENT DOCUMENTS

| | | |
|---|---|---|
| 72222 | 2/1983 | European Pat. Off. . |
| 226569 | 6/1987 | European Pat. Off. . |
| 3230976 | 2/1984 | Fed. Rep. of Germany . |

OTHER PUBLICATIONS

The Remote Measurement of Traffic Generated Carbon Monoxide, by Lucian Chaney, Journal of the Air Pollution Control Association, vol. 33, No. 3, Mar. 1983.

Advances in In-Situ Gas Analyzing Technology, Harry Lord, presented at the Instrument Society of American Instrumentation & Controls Systems Conf. Cleveland, OH, May 21, 1986.

Self-Validating In-Situ NDIR Analyzer, Hary Lord, the Syconex Corporation, Duarte, CA.

A New NDIR Analyzer Incorporating a Complete System Calibration, Harry Lord, H. Jack Maier, The Syconex Corporation.

Brochure, Syconex Corporation, Model 6000 Gas Analyzer.

Confidential Proposal for Development of Remote Emissions Measurement Device for Vehicle Enforcement, Air Quality Products, Inc. 1987.

Brochure, MUTEK, Modular Diode Laser System.

Primary Examiner—Janice A. Howell
Assistant Examiner—Richard Hanig
Attorney, Agent, or Firm—Knobbe, Martens, Olson & Bear

[57] ABSTRACT

A remote gas analyzer for motor vehicle exhaust emission surveillance in which a planar array of gas analyzer beams intersects substantially an entire cross-sectional segment of an exhaust gas plume in order to determine the volume concentration of gas pollutants in the exhaust. In a further variation using more readily available equipment to detect the less prevalent pollutants, the planar array determines the change in amount per unit volume of a first pollutant emitted by a motor vehicle passing the array. The first pollutant having a relatively high and more easily detectable concentration. A second, multi-spectral gas analyzer beam intersects the exhaust to determine the change in concentration of the less prevalent pollutants with respect to ambient, and also determines the change in concentration of the first pollutant. The ratio of the change in the first pollutant's weight per unit volume to its change in concentration as determined by the second analyzer is used to determine the change in the amount per unit volume of the remaining pollutants.

21 Claims, 4 Drawing Sheets

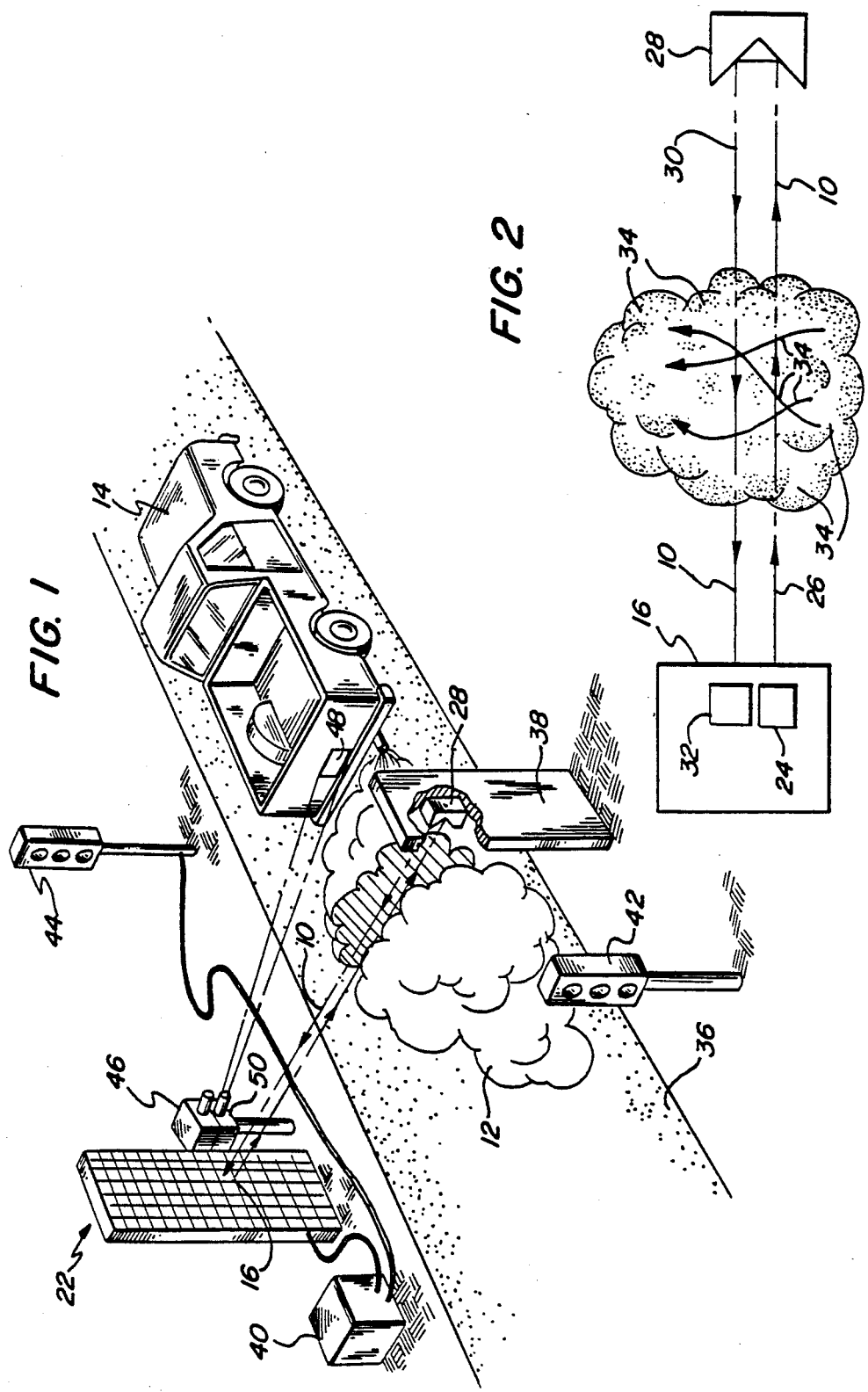

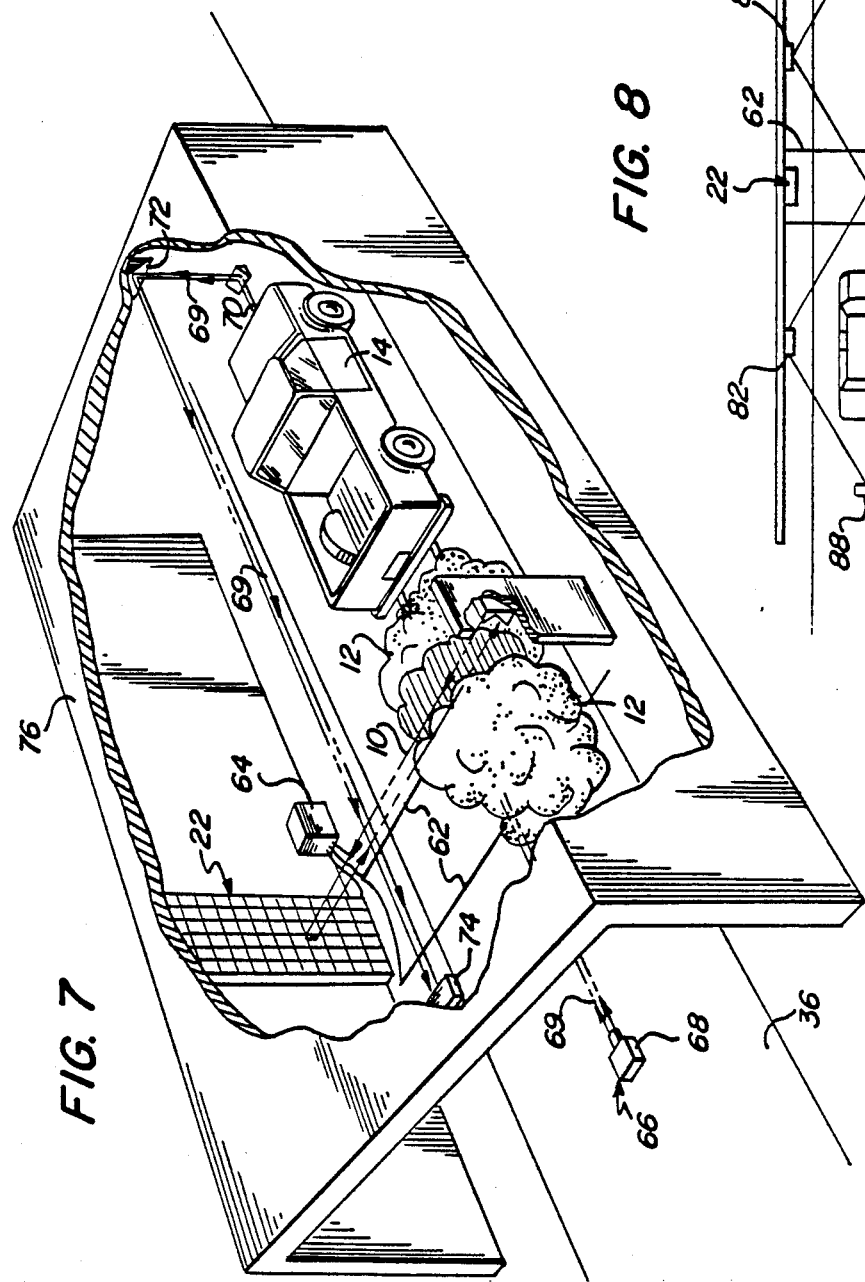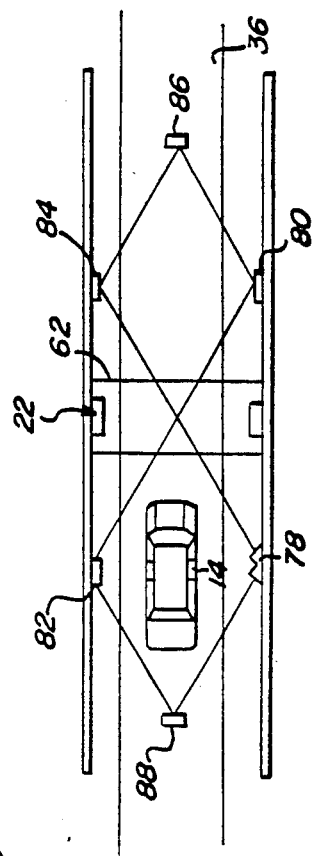

REMOTE GAS ANALYZER FOR MOTOR VEHICLE EXHAUST EMISSIONS SURVEILLANCE

RELATED APPLICATION

This application is a continuation-in-part application of Ser. No. 057,293, filed June 2, 1987, by the same inventive entity.

This invention relates to the measurement and control of exhaust emissions from motor vehicles, and in particular to a gas analyzer system for monitoring and measuring the quantity of exhaust emissions emitted by a moving vehicle in terms of mass units per distance travelled.

BACKGROUND OF THE INVENTION

One of the leading contributors to air pollution is the internal combustion engine which is used to power all types of motor vehicles, be they cars, trucks or motorcycles. Exhaust from the engines in these vehicles contains various pollutants, such as carbon monoxides, nitrous oxides, unburned hydrocarbons, aldahydes and particulate contaminants.

The Federal Government requires that all vehicles sold and registered for use on the highways must meet specific standards as to the amount of pollutants emitted in the vehicle exhaust. Many states, including California, have initiated mandatory inspection and maintenance procedures during which the pollutants in the vehicle exhaust are monitored and compared with predetermined standards. If the vehicle emissions fail to meet these standards, the vehicle must be repaired so the emission standards are met. In California, the process is referred to as a "smog check," and various service stations or smog check stations are authorized to check the vehicle emissions to see if they meet the state imposed requirements.

State and Federal new vehicle emission standards and control requirements are stated in "grams per mile." Several test procedures have been developed to indicate the pollutants in the exhaust gas, and to extrapolate the "grams per mile" from the test procedures. One such method is the constant volume sample test (CVS test) which is included in the Federal Test Procedure that is required for new vehicle certification. This test measures vehicle exhaust emissions under simulated dynamic conditions such as a vehicle would normally experience. The results of this procedure are the measurement of vehicle mass emissions in terms of grams per vehicle mile travelled. In order to accomplish this measurement, the entire exhaust stream emitted from the vehicle is captured via the "CVS" system, and a representative sample is collected for analysis. During this test, the vehicle is operated on a dynamometer to simulate the vehicle traveling a predetermined distance. Knowledge of this distance, and specific exhaust volume produced, with measurement of a proportional sample of exhaust gas concentrations, enables a quantitative calculation of emissions to be expressed as "grams per mile." The CVS test is an exacting, time consuming, and expensive process costing up to one thousand dollars per test, making the test unsuitable for use in more than a limited number of tests on a limited number of vehicles.

Inspection and maintenance programs for monitoring and controlling vehicle emissions on existing vehicles have employed emission testing processes which are less costly than the CVS test. These processes, however, are far less accurate since they do not even attempt to measure vehicle mass emissions under the dynamic conditions which the vehicle typically experiences. Several processes have been suggested or used. The one process in greater use is the "idle" test procedure, which monitors vehicle emissions at idle speeds while the vehicle is stopped. These idle tests typically determine the concentration of various constituents of the exhaust gas, in parts per million (PPM). These tests do not attempt to correlate the exhaust gasses to the actual mass emissions of the vehicle, as in a grams per mile measurement. The PPM measurement has been found to relate to vehicle equipment malfunctions and is thus useful in determining the gross emission characteristics, and to predict failure of vehicle equipment affecting the vehicle exhaust emissions.

The idle emission standards are typically set at limits sufficiently high to accommodate equipment errors, operator errors, and calibration errors. Since idle emissions only "relate" to actual operating emissions, high limits must be set in order to avoid incorrectly failing vehicles. The result of this process is that many vehicles with faulty or substandard emission equipment, escape the test and maintenance requirements and continue to operate with high emissions which pollute the environment.

A short form dynamic measurement process, sometimes called a "loaded mode test" has been proposed as a more accurate testing technique for verifying vehicle emissions in the field for inspection and measurement purposes. This test is performed on a dynamometer, and measures exhaust emission concentrations at idle speeds, and also at higher speeds and vehicle loads. Although more efficient in determining component failures, there is no accurate measurement of the actual mass emissions in the vehicle exhaust. Further, while superior to the "idle test," many vehicles would still escape necessary maintenance and pollute the environment. A further drawback, is the high cost of the testing equipment, such as chassis dynamometers, and exhaust analyzers, which require a high monetary investment for each test station. Further, the loaded mode tests require a larger amount of time to conduct for each vehicle (up to 20-30 minutes). Since there are some 12 million vehicles in California alone, a smog test system is needed that can process several cars per minute, not just a few cars per hour.

Currently in California, the smog check is performed by hooking up a test analyzer system to the exhaust pipe of a vehicle in order to measure the pollutants. This test process samples the exhaust emissions only at idle speeds and is therefore less comprehensive than a dynamic test condition. The smog check can be performed at any of a large number of authorized service stations or smog check stations, but still requires a considerable amount of time and results in inconvenience for the vehicle owner, especially since most smog check stations make you leave the vehicle so the smog check can be performed at the convenience of the station operator, rather than at the convenience of the vehicle owner. Tampering studies have shown that smog check requirements are being circumvented by disconnecting the smog control equipment on the vehicle except when needed for the smog check.

There is thus needed a device which can analyze the pollutants in a vehicle exhaust quickly and cheaply, without causing the vehicle owner to wait an extended period of time, and which further produces results which are more accurate and more tamper-proof.

Most smog checks also have a further disadvantage in that the engine is not being run in a loaded mode when the smog check is taking place. The largest percentage of pollutants are produced during the acceleration of a vehicle rather and maintaining a constant velocity under load, than in stationary idle. Thus, if the smog check is run with vehicles stationary, the transmission not engaged, and no load exerted on the engine, the smog check does not accurately measure the engine pollutants during normal vehicle operation. A device is thus needed to measure the exhaust pollutants during a realistic operation period of the vehicle.

SUMMARY OF THE INVENTION

A means for quickly and efficiently identifying the type and mass of emission pollutants in an exhaust plume of a moving motor vehicle under actual operating conditions is provided. An absorption spectroscopy system is used to determine the amount per unit volume of pollutants in an exhaust plume from a motor vehicle. The system includes a first means for generating a first plurality of optical beams suitable for use in absorption spectroscopy. The beams are arranged to form a first planar array of beams covering a substantial portion of a predefined space. The space is sufficiently large to contain a total cross section of an exhaust plume generated by a motor vehicle passing through the space. The width of the beam array is known, and a timer allows determination of the speed at which a moving motor vehicle passes through the array of beams. The system further includes a first means for detecting the first plurality of beams after they have passed through the exhaust plume at least once. The system further includes a computer communicating with the first generating and detecting means for analyzing the spectral content of the first plurality of optical beams in order to determine the concentration of preselected compounds contained in the exhaust plume passing through said space. The computer can then calculate the quantity of emission compounds in terms of quantity of pollutants per distance travelled by the motor vehicle, by use of the concentration, the vehicle velocity, and the volume enclosed by the array of beams.

This invention can be used in a smog check station for determining the amount of a predetermined number of pollutants contained in the exhaust of a moving vehicle, where the smog check station includes a plurality of spectrum gas analyzers arranged to generate an array of substantially parallel beams across a predetermined space, such that an exhaust plume from a moving motor vehicle passing through said space passes through said array of beams, the array of beams being sized and located such that said beams intersect substantially all of a cross-sectional segment of said exhaust plume. The smog check station further includes a computer communicating with the gas analyzers to determine the amount of a predetermined number of pollutants which are contained in that portion of the exhaust plume intersected by said array of beams.

This invention also provides a method of measuring pollutants in a motor vehicle exhaust plume, including the steps of passing beams of light through a predetermined space, positioning a motor vehicle in proximity to said predetermined space so that an exhaust plume generated by said motor vehicle passes through said space, directing the beams through said exhaust plume such that substantially the entire cross-sectional segment of said exhaust plume is intersected by said beams, and analyzing the beams after passing through the exhaust plume by absorption spectroscopy to detect pollutant concentrations in said plume.

To the above ends, a plurality of gas absorption analyzers cooperate with a plurality of retro-reflectors to form an array of beams which define a predetermined volume. Preferably, a planar array is used. A motor vehicle is operated so as to cause the exhaust plume from the motor vehicle to enter this array of beams, preferably by having the motor vehicle drive through the array of beams. The beam array is large enough to substantially cover an entire cross section of the exhaust plume. A computer, hooked up to the gas absorption analyzers identify the type and amount of a predetermined number of gases (such as HC CO, $CO_2$, and NO) in the exhaust plume. This information can be compared with predetermined standards in order to determine whether the motor vehicle meets applicable requirements for pollutant levels in the exhaust. The measurements also allow the calculation of the mass of pollutants per unit volume.

In one illustrated embodiment, the array of beams from the gas analyzer is placed so as to transverse a roadway from side to side, although in a further embodiment the beams run perpendicular to the roadway, with elements of the beam transfer network being embedded in the roadway. It is further believed possible to have a planar array of horizontal beams, to form a three-dimensional beam matrix which would capture an entire volumetric cross section of the exhaust plane.

In a further embodiment of this invention, the amount of pollutants per unit volume is determined from a ratio method based on the increase in the measured amount and concentration of a first gas. The apparatus for this embodiment comprises the first array of emitters and detectors suitable for use in absorption spectroscopy positioned on opposite sides of said path down which said motor vehicle may pass, with the emitters and detectors positioned so that beams emitted by said emitters intersect substantially an entire cross-sectional area of said exhaust plume along a predetermined length of said exhaust plume. The first array detects a first pollutant.

A second gas analyzer emitter and detector is orientated so that a second beam emitted by the second emitter passes adjacent the moving motor vehicle. The second beam intersects the exhaust plume as it mixes with the atmosphere along a path length sufficient to allow determination of the increase in concentration of a plurality of pollutants emitted by said exhaust plume relative to the concentration before the exhaust from the motor vehicle intersected said second beam. One of the plurality of pollutants is the first pollutant.

A computer takes the data from the array of emitters and detectors, and using absorption spectroscopy, determines the relative increase in the amount per unit volume of the first predetermined pollutant contained in that portion of the exhaust plume intersected by the array. The relative increase is determined with respect to the amount of the first pollutant before the exhaust from the motor vehicle entered the first array.

The computer further determines the relative increase in the amount per unit volume of the plurality of gases other than said first pollutant by using the ratio of the relative increased amount of the first pollutant with respect to the increased concentration of the first pollutant. The ration is multiplied by the relative increase in the concentration of each of the plurality of gases to determine the amount per unit volume.

In a variation on the above, means are provided for determining the velocity of said motor vehicle as it passes the first array. By using this velocity measurement, the computer can determine the amount of pollutants per unit of distance traveled.

Advantageously, during these measurements in this last embodiments, there is provided means for enclosing the first array, the second gas analyzer and the motor vehicle exhaust sufficiently to inhibit environmental disturbances from dispersing the motor vehicle exhaust sufficiently to adversely inhibit the measurement of the amount and concentration of the exhaust gas constituents.

There is thus provided a means of checking the pollutants in an exhaust from a vehicle as the vehicle is moving. Since it is a dynamic measurement, the accuracy of the measurement is increased. The motor vehicle operator need only "drive through" the array of beams, so the time of the vehicle operator and tester is greatly reduced. A large number of motor vehicles can be checked in a very short period of time, thus permitting an increase in the frequency of the checks, and a lowering of the time which the motor vehicle operator needs to spend to get the vehicle checked. The large number of tests that can be run in a short time period lowers the cost, thus benefitting the vehicle owner, while maintaining the public health by reducing pollutants.

BRIEF DESCRIPTION OF THE DRAWINGS

The above, and other advantages of this invention will become more apparent, especially to one skilled in the art, when considered in connection with a detailed description of a preferred embodiment described in connection with the following drawings, in which like numbers refer to like parts throughout the drawings.

FIG. 1 is a perspective view of an embodiment of this invention with gas analyzer beams generally horizontal, and parallel to the roadway;

FIG. 2 is a schematic illustrating a dual path, spectral gas analyzer;

FIG. 7 is a perspective view of a further embodiment of this invention using an array and a second gas analyzer enclosed in a tunnel; and FIG. 8 is a top plan view of an optical beam arrangement suitable for use in the invention shown in FIG. 7.

DETAILED DESCRIPTION OF THE ILLUSTRATED EMBODIMENTS

Figure 3:
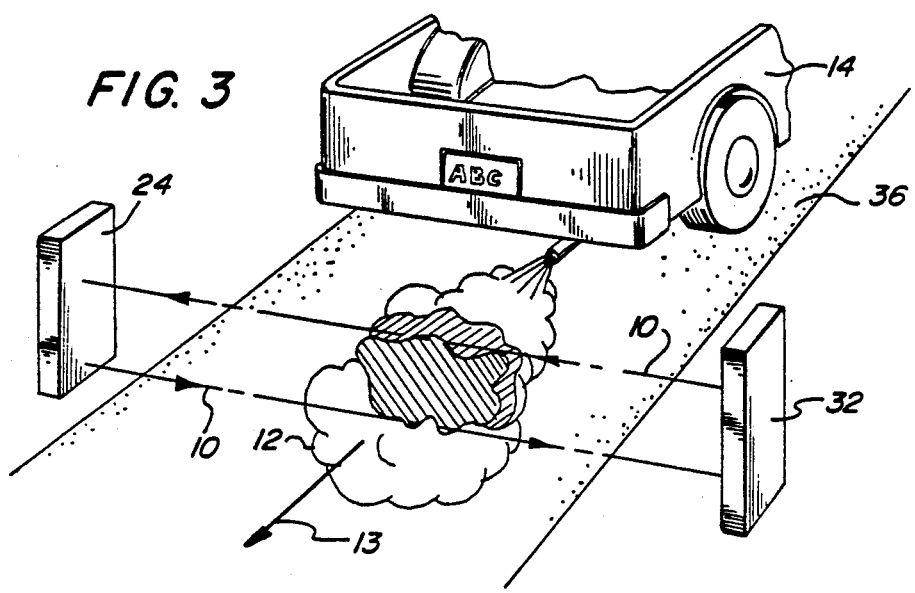
FIG. 3 is a simplified view of an exemplary gas analyzer array and an exhaust plume.

Referring to FIG. 1, a gas analyzer array 22 comprises a plurality of gas absorption analyzers 16, each of which emits a light beam 10. The gas analyzer array 22 is placed on one side of a road 36. On the opposite side of the road 36, is a retro-reflector array 38, comprised of a plurality of individual retro-reflectors 28 (FIG. 2). The gas analyzer array 22 and the retro-reflector array 38 are aligned and cooperate such that the beam 10 from a particular gas analyzer 16 in the array 22 is returned to the same gas analyzer 16 that emitted the beam 10. The arrays 22, 38 are arranged such that the beams 10 form a pattern which encompasses substantially an entire cross-section of an exhaust plume 12 from a motor vehicle 14. The beams are detected by the gas absorption analyzers 16 of the array 22 to determine the amount of pollutants in the exhaust plume 12. The information on the amount of pollutants from the gas absorption analyzers 16 may be combined with the information from the character recognition device 46 and recordation device 50 so as to provide a tamper proof record of a particular set of pollutant data from the motor vehicle 14. Preferably, a character recognition device 46 and a character recordation device 50 are oriented so as to view an identification plate containing identifying information, such as license plate 48, placed on motor vehicle 14.

The gas absorption analyzers 16 work on the principal that molecules of different materials absorb light at specific wavelengths or sets of wavelengths characteristic of those molecular compounds. The amount of light absorbed is directly proportional to the concentration of the molecules or compounds present. The process is commonly known as absorption spectroscopy.

Several types of gas analyzers have been developed on this absorption spectroscopy principal, such as the non-dispersive infrared (NDIR) technique, the non-dispersive ultraviolet (NDUV) technique, and the gas filter correlation (GFC) spectroscopy technique. An explanation of the NDIR system can be found in an article by Lord, H.C. and Maier, H.J., "a new NDIR analyzer incorporating a complete system calibration," ISA analysis instrumentation 20, Chicago, Ill., May, 1984, which is incorporated herein by reference. A version of a currently available NDIR gas analyzer is described in a brochure on the model 6,000 gas analyzer by Syconex Corporation, 433 West Alan Avenue, San Dimas, Calif. 91773-1443, which brochure is hereby incorporated by reference. A description of the GFC spectroscopy apparatus, and particularly one which was used to determine the amount of carbon monoxide in vehicle exhaust is described in an article by Lucin W. Chaney, "The Remote Measurement of Traffic Generated Carbon Monoxide," Journal of the Air Pollution Control Association, 220-22 (1983), which is also incorporated herein by reference.

Referring to FIG. 2, each gas absorption analyzer 16 in the array 22 (FIG. 1) comprises an emitter 24 which emits a signal, such as optical beam 10, along a first path 26 towards a retro-reflector 28. The retro-reflector 28 causes the signal transmitted on the first path 26 to be displaced and returned along a substantially parallel second path 30, toward a receiver or detector 32 located adjacent the emitter 24. The gas absorption analyzer 16 is spaced apart from the retro-reflector 28 and positioned such that pollutant particles 34 from an exhaust plume 12 of a motor vehicle pass through the first and second paths 26 and 30 such that each of the beams 10 from the gas analyzers 16 in the array 22 (FIG. 1) makes two passes through the exhaust plume 12. This two pass configuration will be referred to as "dual path" analyzer.

In the embodiment shown in FIG. 1, the gas absorption analyzers 16 are each dual path analyzers which have a beam width of approximately three inches. Preferably, the analyzers 16 are multiple gas analyzers which means that a single beam can analyze several gases. A six gas analyzer may be advantageously used. The beams 10 should be exposed to the exhaust plume 12 for a sample time of at least 20 milliseconds before a reading on the amount of the six pollutants is obtained from the analyzer 16. A relatively larger diameter on the retro-reflectors 28 (e.g., 5 inches) is believed desirable to facilitate alignment.

A computer 40 is in communication with the gas analyzer array 22 and serves to analyze the beams 10 of the array 22, according to the particular method of absorption spectroscopy being used.

As a motor vehicle 14 travels along the road 36, the exhaust plume 12 passes through the array of beams 10 formed by the gas analyzer array 22 and the retro-reflector array 38. The array of beams lo is located so as to transverse substantially the entire cross section of the exhaust plume 12 during the time the gas analyzers 16 are operating to measure the pollutants in the exhaust plume 12. Preferably, the array of beams 10 is substantially orthogonal to the longitudinal axis 13 (FIG. 4) of exhaust plume 12. The gas analyzer array 22, in communication with the computer 40, measures the quantity of various pollutants in the exhaust plume 12. The constituents measured would preferably include carbon monoxide (CO), carbon dioxide ($CO_2$) nitrogen oxide (NOX) and opacity. The particular pollutants to be measured would be predetermined.

The array of beams 10 provides a means of capturing the entire representative exhaust product of the exhaust plume 12 that is contained in a known volume of space. Preferably, the array of beams 10 is planer. As used herein, a "planar array" refers to an array of elements such as emitters 24, retro-reflectors 28, or beams 10, while there are a plurality of adjacent elements along each of two orthogonal directions. As shown in FIG. 1, the gas analyzers 22 form a planar, rectangular array of gas analyzers 16.

As shown in FIG. 3, the beams 10 intercept a planar cross sectional slide 11 of the exhaust plume 12, so as to get a representative sample of the entire exhaust plume 12 and thus minimize distortion in pollutant measurements that could occur from nonuniform dispersion or distribution of the pollutants in the exhaust plume 12. It is preferably that the analyzed cross-section of the exhaust plume 12 comprise a planar section that is substantially perpendicular to the path of the exhaust gases after they exit the exhaust pipe of the motor vehicle. Accordingly, as shown in FIG. 3, the beams 10 are oriented so that the slice 11 is perpendicular to a longitudinal axis 13 of the exhaust plume 12. The volume of the slice 11 is a function of the size or diameter of the beams 10, the thickness of the light beam array, less any space between the beams 10, and the shape of the plume 12.

Since the system functions with moving motor vehicles 14, the movement causes the exhaust plume 12 to be dispersed along a line substantially parallel to the length of the road 36. Thus, the array 22 is preferably orthogonal to the axis 13 so the cross section 11 of the exhaust plume 12 intersected by the array 22 contains a representative sample of pollutants. Since the exhaust plume 12 expands after it exits the motor vehicle 14, a smaller array 22 can be used if the pollutants are measured soon after the vehicle 14 passes.

Previous gas analyzer devices did not attempt to take a cross-sectional measurement of the exhaust plume 12, let alone capture a representative cross-sectional volume sample of exhaust plume 12. The use of an array of beams 10 helps nullify the effects of environmental and operational factors such as vehicle speed, ambient wind disturbances, turbulence caused by the movement of the vehicle 14, and other temperature and environmental disturbances. The accuracy produced by using a single beam 10 which passes twice through the exhaust plume 12 can be affected by any of these factors, as for example, if the beam 10 is located below the level of the exhaust pipe of the vehicle 14, or if there is severe wind which causes the lighter pollutant compounds of exhaust plume 12 to move away from the single beam 10. Thus, it is preferable to utilize multiple beams 10.

The gas analyzer array 22 is illustrated as being a planar array, in this case a rectangle having dimensions of approximately four feet horizontal, by ten feet vertical. The retro-reflector array 38 is also a planar array, with a rectangular shape. The beams 10 provide about 50% or more area coverage of the 4×10 array, since some space occurs between the beams 10.

The dimension of the array parallel to the road 36 is selected to be sufficiently large that the pollutants in the exhaust plume 12 are exposed to the array of beams 10 for a sufficient time to allow the gas analyzers 16 to identify and measure the amount of predetermined gases in the beams 10. This dimension will vary depending on the sampling time needed by the gas analyzers 16, the speed of the motor vehicle 14, the turbulence of the air, and the resulting dilution and expansion of the exhaust plume 12.

The array dimension perpendicular to the road 36 is selected to be large enough to allow the beams 10 to intersect substantially the entire cross-sectional segment of the exhaust plume 12 during the analysis of the pollutants in the plume 12, even allowing for expansion of the plume 12. Thus, the dimensions of the arrays 22 and 24 are sufficiently large to allow the gas analyzers 16 to identify the pollutants in the exhaust plume !2, and measure the concentration of pollutants in the portion of the plume 12 intersected by the beams 10. Since the volume of the beams 10 is known, and since the beams 10 intersect a total cross-section of the exhaust plume 12, the amount of pollutants, in terms of weight or mass, in the volume of the beams 10 can be calculated by computer 40.

The interruption of two horizontally adjacent beams 10 by the passage of the motor vehicle 14 allows timing the speed with which the motor vehicle 14 passes through the array of beams 10. Alternately, a separate timer (not shown) could be used to determine how long it took the vehicle 14 to pass a known distance. The time to pass the sensors, and the distance between the sensors can be used to calculate the velocity of the motor vehicle 14.

The pollutant data from a known segment of the exhaust plume 12, when combined with the speed of the motor vehicle 14, allows the computer 40 to calculate the grams per mile of specified pollutants contained in the exhaust plume 12.

Figure 4:
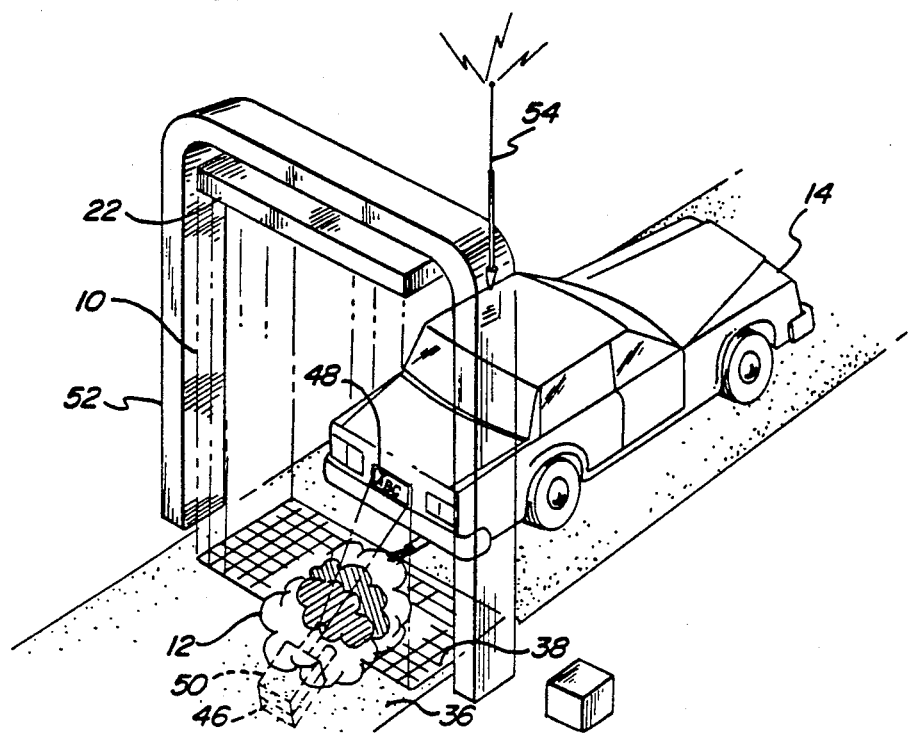
FIG. 4 is a perspective view of an embodiment of this invention with gas analyzer beams substantially perpendicular to the road.

Referring to FIG. 4, there is shown an alternate embodiment which has the beams 10 in a substantially vertical orientation. The retro-reflector array 38 is located beneath the motor vehicle 14 by being placed in the road 36. The gas analyzer array 22 is located above the road 36 and is supported in that location by a support 52. The gas analyzer array 22 is spaced apart from the retroreflector array 38 sufficiently that a motor vehicle 14 can pass between the arrays 22 and 38 so that an exhaust plume 12 of the motor vehicle 14 can be contained and analyzed by the array of beams 10. Again, the array of beams 10 formed by the gas analyzer array 22 is preferably orthogonal to the longitudinal axis 13 (FIG. 5) of the exhaust plume 12. A character recognition device 46 and character recordation device 50 is placed under the surface of the roadway 36 so as to view the license plate 48 of the passing motor vehicle 14. The time it takes the motor vehicle 14 to pass through two horizontally spaced beams 10 can be used, with the known spacing between those beams 10, to allow the computer 40 to determine the speed of the motor vehicle 14.

In a further variation of this invention, the computer 40 is in electronic communication with a remotely located computer by means of the data receiving and transmission antenna 54. The antenna 54 allows the computer 40 to gain access to information in remotely located motor vehicle files, which may be retained at the State's Department of Motor Vehicles. Conversely, pollutant information on a particular motor vehicle 14 can be sent to a remotely located Department of Motor Vehicles, via antenna 54, so that the Department of Motor Vehicles can use the information on the vehicle emissions by, for example, sending a notice to the motor vehicle owner or refusing to issue a new vehicle registration until the vehicle owner has the vehicle emissions changed to meet predetermined standards.

Figure 5:
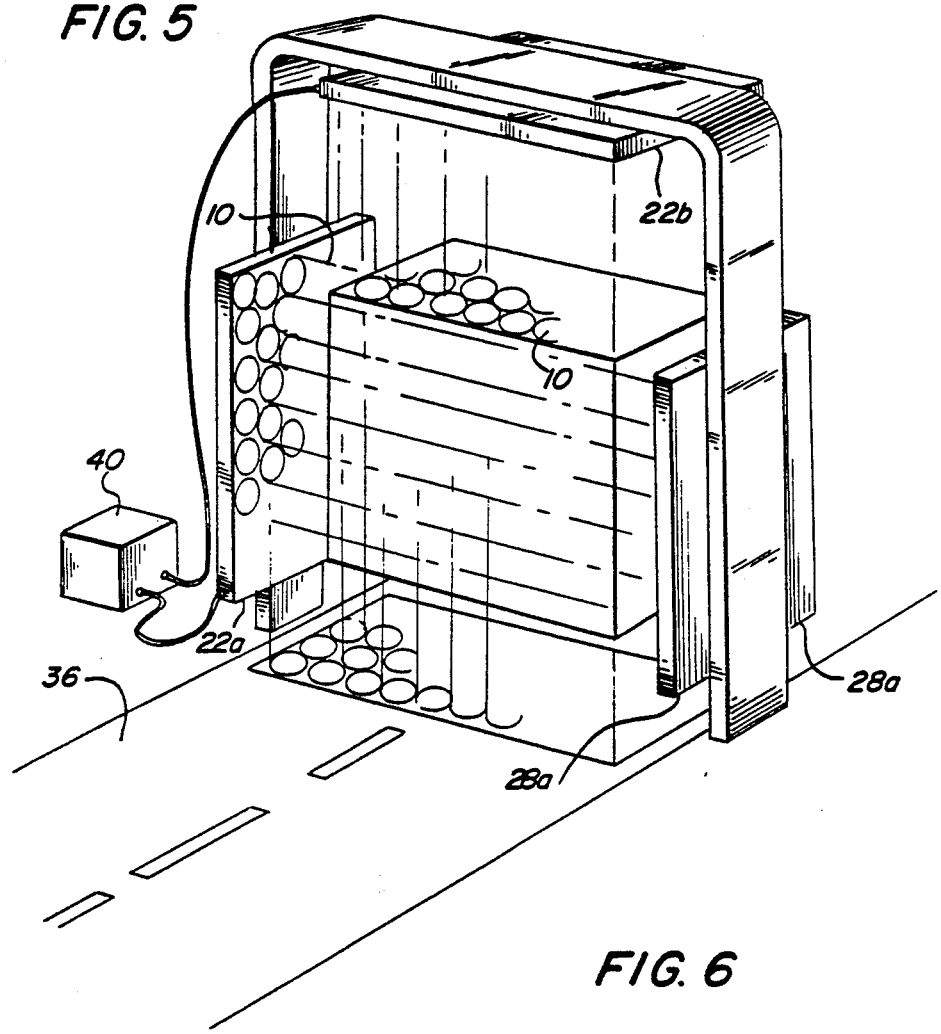
FIG. 5 is a perspective view of an embodiment of this invention with a three-dimensional matrix of gas analyzer beams.

FIG. 5 shows yet another embodiment of this invention. A first array of gas analyzers 22a generates a first array of beams 10 that are substantially parallel to the road 36. A corresponding first array of retroreflectors 28a returns these beams 10 to the gas analyzers 22a in a double path gas analyzer configuration. Preferably, the array is a planar array having plural emitters in each of the two orthogonal directions corresponding to its length and width.

A second array of gas analyzers 22b generates a second array of beams 10 that are substantially perpendicular to the road 36. A corresponding second array of retroreflectors 28b returns these beams 10 to the gas analyzers 22b in a double path gas analyzer configuration. Preferably, the array is a planar array having plural emitters in each of the two orthogonal directions corresponding to its length and width.

The first and second arrays of beams 10 intersect to form a three dimensional matrix of beams 10, which is positioned so that the exhaust plume 12 (FIG. 4) passes through the matrix. Again, the matrix of beams 10 is preferably large enough, and positioned such that it contains substantially all of a cross sectional segment of the exhaust plume 12. Preferably, the beams 10 are substantially orthogonal to the longitudinal axis 13 (FIG. 5) of exhaust plume 12. The apparatus functions in a manner analogous to the prior embodiments, except that two arrays of beams 10 and intersecting the exhaust plume 12 in stead of only one array.

In FIGS. 1 and 2, the gases absorption analyzers 16 were shown as a two-path analyzer. It is possible, however, that a single-path analyzer could be used as shown in FIG. 5. In the case of a single-path analyzer, there is no retro-reflector, and the plurality of emitters 24 emit an array of beams 10 towards the array of receivers 32 which, in this case, would be spaced apart from the array of emitters 24 sufficiently so that an exhaust plume 12 from a motor vehicle 14 could pass through the beams 10.

Figure 6:
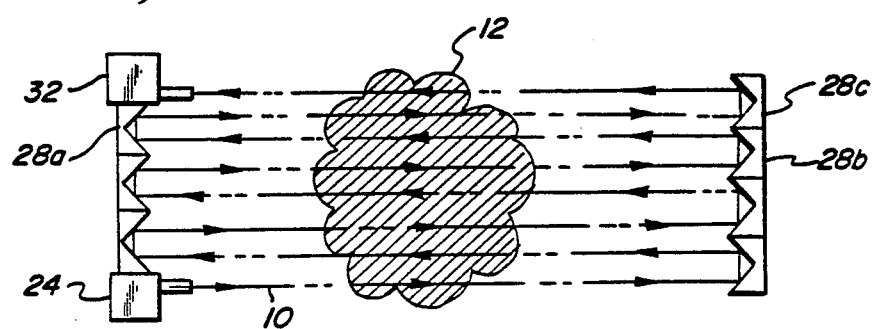
FIG. 6 is a schematic view of an exemplary multiple path gas analyzer system.

Referring to FIG. 6, in a further embodiment of this invention, a multiple path beam 10 can be used which is greater than the dual path previously described. In essence, a plurality of beams 10 can be generated by a single emitter 24. In the embodiment of FIG. 6, an emitter 24 and detector 32 are separated by a first retroreflector 28a. A second and third retro-reflectors 28b and c, respectively, are located on opposite sides of an exhaust plume 12, and aligned with respect to the first retro-reflector 28a, and the emitter 24 and detector 32, such that a beam 10 from the emitter 24 is folded or reflected a plurality of times before being received by the receiver 32. By increasing the number of retro-reflectors 28, the path of the beam 10 can be folded a plurality of times as long as the retro-reflectors 28 are suitably aligned. By varying the number of times the path of the beam 10 crosses the exhaust plume 12, the number of gas absorption analyzes 16 can be varied.

In operation, the gas analyzer array 22, such as that of FIG. 1, analyzes the mass of pollutants contained in the intersected volume of exhaust plume 12. The system determines whether the motor vehicle 14 meets predetermined requirements, such as smog requirements imposed by state law. The system also identifies the relative amount of pollutants in the exhaust plume 12 so that the identified motor vehicle 14 can be requested to undergo further testing or repair at an approved station.

Since the analysis is done while the motor vehicles 14 are in operation, rather than sitting still, the analysis is done under a dynamic load and the accuracy of the analysis is enhanced. Further, the time needed to analyze the pollutants is greatly minimized since there is no need to open the hood, and connect and disconnect and analyze the apparatus. Since the motorist is merely required to "drive through" the test system, a large number of motor vehicles can be processed in a shorter amount of time, thereby reducing the cost to run the test system and reducing the inconvenience to the owner of the motor vehicle.

Further, the beams 10 are interrupted when the motor vehicle 14 passes through them. By timing the disruption of the beams 10 by the motor vehicle 14, as, for example, when the rear of the vehicle passes out of the respective beams 10, the speed of the motor vehicle 14 can be determined. The vehicle speed, vehicle weight and pollutant content of the exhaust plume 12 can provide a much more accurate gauge of whether or not the motor vehicle 14 meets the applicable smog requirements set by local law.

The short test time and ability to automate the testing provides unexpected advantages not previously possible. By implementing the test system on public roadways, such as freeway on-ramps, and automating the test procedure by use of character recognition devices, motor vehicles can be continuously tested for smog compliance. The constant, and even random testing made possible by the test arrangement will further compliance with the air quality requirements, and improve air quality.

The above embodiments have the disadvantage of requiring highly accurate and sensitive equipment in order to accurately determine the amount of some of the less abundant pollutants contained in the exhaust plume 12. The path length of beam 10 within the exhaust plume 12 must be sufficiently long to obtain an accurate reading of pollutants that sometimes have concentrations on the order of a few parts per million within the exhaust plume, and a few parts per billion when dispersed in the atmosphere. To allow the use of less sensitive equipment which is more readily available, and to allow the use of shorter path lengths within the exhaust plume 12, further embodiments of this invention are presented in FIGS. 7 and 8.

Referring first to FIG. 7, the array 22 is positioned along the route of travel of a motor vehicle 14 and positioned so as to intersect substantially all of a cross-sectional slice of an exhaust plume 12 of the passing motor vehicle 14. In this embodiment however, the array 22 is used to determine the weight or mass amount of only a first, single exhaust gas constituent on a weight or mass per unit volume basis. Advantageously, the single exhaust gas is one having a high concentration, such as carbon dioxide, or more advantageously, carbon monoxide. The array 22 thus acts as a means for determining the weight per unit volume of a single exhaust gas pollutants in the exhaust plume 12. It is known in the art and not described in detail herein, how to use gas concentrations of a known volume to calculate gas measurements in terms of weight per unit volume, or weight per distance travelled.

A speed detector is located adjacent the array 22, and can take various forms known in the art, such as a photo cell. The speed detector in the illustrated embodiment takes the form of two wires 62a and 62b, one on each side of the array 22, and extending across the road 36. The distance separating the wires 62a and 62b is known. As the front tires of the motor vehicle 14 cross each of the wires 62, an electrical impulse is sent to a computer 64. A clock internal to the computer 64 times the intervals between the electrical impulses. The velocity of the motor vehicle as it passed the array 22 can be determined from the distance between the wires 62, and the time it took the front tires of the motor vehicle 14 to pass both of the wires 62.

A second gas absorption analyzer 66 also emits a beam which intersects and detects pollutants from the exhaust plume 12. The second gas analyzer 66 is advantageously a multi-spectral analyzer which has a beam 69 emitted from a plurality of tunable laser heads. The use of tunable lasers allows accurate measurements at specific spectral frequencies. The tunable lasers allows the selection of specific frequencies for pollutants which can avoid any overlapping frequencies of other gas constituents, in order to provide a more sensitive and accurate determination of the pollutants.

The second gas laser 66 detects the concentration of a several exhaust gases, such as nitrous oxides, hydrocarbons, or aldehydes. The concentration of these gases is typically measured in terms of parts per million ("PPM") or parts per billion ("PPB"), and has no weight amount associated with the number as the volume of the space occupied by the gas is unknown. The second gas analyzer 66 also measures the concentration (again in PPM) of the first gas detected by the array 22, which in the illustrated embodiment is carbon monoxide.

In the embodiment illustrated in FIG. 7, the second gas analyzer 66 is a folded-path system oriented along the direction of travel of the motor vehicle 14 along the path or road 36. The second gas analyzer 66 comprises an emitter 68 placed in or on the road 36 so the motor vehicle 14 can pass over the emitter 68 without hitting it. The emitter 68 emits a beam 69. A first reflecting mirror 70 located down the road 36 is aligned to receive and reflect the beam 69 emitted from emitter 66 in a direction perpendicular to the road 36. A second reflecting mirror 72 is located above the first mirror 70 and is aligned to receive and reflect the beam 69 back in the direction of the emitter 68, but at a height above the motor vehicle 14. A detector/receiver 74 is aligned to receive the reflected beam 69 from the second mirror 72 and, communicates with the computer 64 by means known in the art and not shown in detail herein, in order to detect and determine the concentration of the selected exhaust gas constituents in terms of parts per million or parts per billion.

The second gas analyzer 66 thus comprises a means to determine the concentration of selected pollutant gases in that portion of the exhaust plume 12 which intersect the path of beam 69 of the second gas analyzer 66. A total path length for the beam 69 of about 50 meters intersecting the exhaust plume 12, is believed sufficient to provide an accurate reading with the current sensitivity of readily available gas analyzers.

The 50 meter path length within the exhaust plume 12 requires that the path of the beam 69 of the second gas analyzer 66 either be folded multiple times across the width of the exhaust plume 12, or that the path of the beam 69 traverse the length of the exhaust plume 12. The embodiment illustrated in FIG. 7 traverses the length of the exhaust plume 12.

While the second gas analyzer 66 is shown with the path of beam 69 folded in the vertical plane, it is possible to locate the emitter, mirrors and detector/receiver so the path of the beam 69 is folded in the horizontal plane with the beam 69 passing on the sides of the motor vehicle 14. Similarly, a retro-reflector could be used in place of mirror 70 to reflect the beam 69 back to the emitter 66 and thus maintain the beam 69 on one side of the motor vehicle 14. A further reduction in the length could be achieved by folding the path of beam 69 multiple times in either the vertical, horizontal, or both, planes. Depending on the sensitivity of the equipment used, a transverse orientation of the beam 69 could be used wherein the beam 69 passes across the width of the exhaust plume 12 rather than along its length.

To minimize environmental effects on the amount of gases detected by the array 22 and the concentration of gasses sensed by second gas analyzer 66, an enclosure 76 may advantageously be used. The enclosure 76 may take the form of a tunnel, having a length greater than the distance between emitter 68 and the mirror 70. Advantageously, the enclosure 76 is sized to permit safe passage of motor vehicle 14. In order to maintain a higher concentration of the exhaust gases from the exhaust plume 12, however, the enclosure 76 should be as small as safely practicable. An enclosure 76 having a cross-section of about ten feet by ten feet is believed suitable.

The use of an enclosure 76 allows the second mirror 72, and the detector/receiver 74 to be mounted in the ceiling of the enclosure 76. The array 22 is advantageously placed toward the center of the enclosure 76 in order to minimize the effects which the enclosure's entrance and exit openings will have on the movement of gases and air within the enclosure, especially the disturbance caused as the motor vehicle 14 enters and exits the openings of the enclosure 76.

In operation, a motor vehicle 14 passes through the enclosure 76 along path 36, producing an exhaust plume 12 that is temporarily contained in the enclosure 76. A speed of about 35 miles per hour is believed advantageous for the motor vehicle 14. The array 22 determines the change in the weight or amount of the selected exhaust gas constituent in the exhaust plume 12 in such terms as grams per cubic centimeter. The change in weight is relative to the weight before the motor vehicle exhaust plume intersected the array 22. Since the speed of the vehicle 14 is known as it passed the array 22, and since the width of the "slice" in the exhaust plume 12 is known, it is possible to determine (via computer 64) the increase in the amount of the selected exhaust pollutant per distance travelled, in such terms as grams per kilometer, pounds per mile, or grams per mile.

The second gas analyzer 66 determines the change in concentration of a plurality of gases, including the first gas, in terms of parts per million or parts per billion. The change in concentration is relative to the gas concentrations before any gases from the exhaust plume of the motor vehicle being tested intersected the beam 69 from the second gas analyzer 66.

The ratio of the increase in the amount of the first gas detected by array 22, and the increase in the concentration of that same gas as determined by the second gas analyzer 66 is then determined. This ratio reflects a percentage increase from the pre-test amounts of the first gas. This ratio can then be applied to the other increased gas concentrations determined by the second gas analyzer 66 in order to determine mass per unit volume, or advantageously to determine weight per unit volume of each of the other plurality of gases for which the concentration was determined by the second gas analyzer 66. This ratio can also be used to determine the weight per distance for each gas in terms of grams per kilometer, pounds per mile, or grams per mile.

Since current governmental regulations specify acceptable levels of exhaust pollutants in terms of grams per mile, an easy comparison can determine whether the exhaust of the motor vehicle 14 meets the governmental specifications. Advantageously, a computer can determine the amount of the gases and compare them with the government requirements for a written, side by side comparison.

To illustrate a potential test, in which a motor vehicle passes the array 22 at a speed of 35 miles per hour, and the array 22 measures the increase in amount of carbon monoxide as five grams per mile (5 g/mi) over the amount before the vehicle passed the array 22. Second gas analyzer 66 senses a concentration of carbon monoxide of 10 PPM along the path of its beam 69 before the motor vehicle 14 passes, and senses a concentration of carbon monoxide of 11 PPM after the motor vehicle 14 passes for a ten percent (10%) increase in carbon monoxide. This 10 % increase in carbon monoxide corresponds to a five gram per mile increase in the amount of carbon monoxide.

If the second gas analyzer 66 measured the concentration of another gas, say Nitrogen Oxide, as being 1 PPM at ambient, and 1.01 PPM (10 ppb) after the motor vehicle 14 passed, for a one percent (1%) relative increase in Nitrogen Oxide, then the amount of Nitrogen Oxide per mile in the exhaust is determined as:

$$((5 \text{ g/mi})/(10\%))(1\%) = 0.5 \text{ g/mi}$$

The relatively small increase in the plurality of gases such as Nitrogen Oxide (10 ppb) inhibits using the array 22 to determine the amount of that gas per mile using readily available equipment. However, the concentration of a gas on the order of 3 ppb can be determined by readily available equipment using the described embodiment of the invention. The ratio of the relative increases, based on the absolute amount of a more prevalent gas, thus provides a means to determine the weight amount of gas added by the exhaust of a motor vehicle 14 during operation of that motor vehicle.

Since the measurements of the amounts and concentrations of the gas pollutants can be done on a relative basis with respect to the pre-existing amounts and concentrations, the presence of residual gas pollutants from ambient conditions or from prior motor vehicles 14 should not affect the accuracy of the measurements and calculations. The residual background level of pollutants is effectively nulled out by using the relative increase in the amount of gases and the relative increase in gas concentrations. As is apparent from the above, this method of determining the amount of gases thus assumes that the gases are dispersed equally in the exhaust plume as it dissipates and mixes with the ambient air.

Since it is a relative measurement, it is not essential that the beam 69 of the second gas analyzer 66 actually intersect the exhaust plume 12 as it exits the motor vehicle 14; it need only intersect a sufficient path length of the surrounding air intermixed with the exhaust plume to measure the relative increase in concentration of the exhaust gas constituents. It is advantageous, however, to arrange the array 22 and second gas analyzer beam 69 to try and pass through the portion of the exhaust plume 12 having the highest concentrations of pollutants when the respective pollutant readings are made.

A further variation of the path length of the gas analyzer beam is shown in FIG. 8, which is taken looking down on road 36, with "down" being designated as the direction of travel of the motor vehicle 14, which is from left to right in FIG. 8. An emitter/receiver 78 is located adjacent the edge of the path 36, about one-fourth (¼) of the way down the length of the enclosure 76. A mirror 80 is located on the same side of the path 36 as the emitter/receiver 78, about three-fourths (¾) of the way down the length of the enclosure 76. Opposite the emitter/receiver 78 is a mirror 82, located on the other side of path 36. Opposite the mirror 80, on the other side of the path 36, is located a mirror 84. At the center of the path 36 are located two additional mirrors 86 and 88, which face each other. The mirror 86 is located down the path 36 a distance equal to about half the distance between mirror 80 and the emitter/receiver 78. The mirror 88 which faces mirror 86, is at a distance from mirror 86 equal to about twice the distance between mirror 80 and emitter/detector 78.

In operation, the mirrors 80, 82, 84, 86 and 88 are aligned with the emitter/receiver 78 so that the path of a beam 90 from emitter/receiver 78 forms two diamond patterns, end to end, across path 36, with the beam 90 originating with emitter/receiver 78, and ending with emitter/receiver 78. Each diamond pattern is large enough to encompass a motor vehicle 14 without interrupting the diamond path of beam 90. As the motor vehicle 14 passes down the path 36, the beam 90 is interrupted except when the motor vehicle 14 is at the center of the two diamonds formed by the path of beam 90. Thus, the beam 90 completes its circuit twice for each time the motor vehicle passes down the path 36, thus providing two readings of the gas pollutants which may be accurately collated with the position of motor vehicle 36. Interruptions of the beams can also be used to determine the velocity of the vehicle.

A further variation on this alternate embodiment would be to use the vertical orientation of 22 as shown in FIG. 4, in the enclosure 76 instead of the single array 22. The use of two arrays 22 and 38, as shown in FIG. 5 could also be used with this alternate embodiment as described with respect to enclosure 76 and FIG. 7. A still further, and simpler variation of the alternate embodiment using enclosure 76 would be to replace the array 22 of FIG. 7 with the single emitter 24 as shown and described with respect to FIG. 6.

The invention of this alternate embodiment allows the use of currently available technology to determine the amount of exhaust pollutants of a motor vehicle exhaust during actual operation of the motor vehicle. For example, the concentration of carbon monoxide in the exhaust as it exits the tailpipe of a motor vehicle is on the order of 2000 PPM. When that exhaust plume is expanded or diluted into the enclosure 76, the concentration of the carbon monoxide is on the order of 10 PPM. While the concentration of carbon dioxide $CO_2$ is 13 times greater the other exhaust constituents are considerably lower, and may be more than a hundred times smaller than the concentration of carbon dioxide or carbon monoxide.

The relatively low concentration of many of the exhaust gas constituents inhibits accurate direct measurement of the weight per unit volume by array 22, especially using readily available equipment. Indeed, the longer path length of the second gas analyzer 66 is needed to compensate for the small concentration of the less abundant exhaust gases in the exhaust plume.

The alternate embodiment, however, allows the use of a relatively compact array 22 to determine the mass or weight per unit volume of the most prevalent exhaust constituent, while using a second, multi-spectral gas analyzer to determine the concentration of the less prevalent exhaust constituents along a specified path length. The ratio method to determine the resulting weight of the rarer exhaust gases allows a heretofore unavailable use of existing technology with an accuracy not previously available. The fact that the exhaust constituents can be obtained from a moving motor vehicle 14 further increases the accuracy of the readings and provides an ease of testing not previously available.

I claim:

1. An apparatus for determining the amount of pollutants in the exhaust emitted from a moving motor vehicle traveling along a path, comprising:

a first array of emitters and detectors suitable for use in absorption spectroscopy positioned so the beams emitted by said emitters traverse said path down which said motor vehicle passes, said emitters and detectors positioned so that beams emitted by said emitters intersect substantially an entire cross-sectional area of said exhaust plume along a predetermined length of said exhaust plume, before said beams are received by said detectors, said first array detecting a first pollutant;

a second gas analyzer emitter and detector suitable for use in absorption spectroscopy orientated so that a second beam emitted by said second emitter passes adjacent said motor vehicle, the second beam intersecting the exhaust plume as it mixes with the atmosphere along a path length sufficient to allow determination of the increase in concentration of a plurality of pollutants emitted by said exhaust plume relative to the concentration before the exhaust from said motor vehicle intersected said second beam, said plurality of pollutants including said first pollutant;

a computer in communication with said first array of emitters and detectors to determine the relative increase in the amount per unit volume of said first predetermined pollutant contained in that portion of said exhaust plume intersected by said array, said relative increase being determined with respect to the amount of said first pollutant before said exhaust from said motor vehicle intersected the beams emitted by said first array, said computer further determining the relative increase in the amount per unit volume of said plurality of gases other than said first pollutant by using the ratio of said relative increased amount of said first pollutant to said relative increased concentration of said first pollutant from said second gas analyzer, multiplied by the relative increase in the concentration of each of said plurality of gases as determined from said second gas analyzer.

2. An apparatus as defined in claim 1, further comprising:

means for determining the velocity of said motor vehicle as it passes said first array, and wherein said computer uses said velocity to determine the amount of said pollutants per unit of distance traveled.

3. An apparatus as defined in claim 2, further comprising:

means for enclosing said first array, said second gas analyzer and said motor vehicle exhaust to inhibit environmental disturbances from dispersing said motor vehicle exhaust sufficiently to adversely inhibit the measurement of the amount and concentration of said exhaust gas constituents.

4. An apparatus as defined in claim 2, wherein said emitters emit infrared light.

5. An apparatus as defined in claim 2, wherein said array is a planar array.

6. An apparatus as defined in claim 3, wherein said emitters emit infrared light.

7. An apparatus as defined in claim 2, wherein said first array of emitters and detectors are oriented in planes substantially parallel to the path on which said motor vehicle is traveling.

8. An apparatus as defined in claim 2, wherein said first array of emitters and detectors are oriented in planes substantially perpendicular to the path on which said motor vehicle is traveling.

9. An apparatus as defined in claim 3, wherein said first array of emitters and detectors are oriented in planes substantially parallel to the path on which said motor vehicle is traveling.

10. An apparatus as defined in claim 3, wherein said first array of emitters and detectors are oriented in planes substantially perpendicular to the path on which said motor vehicle is traveling.

11. An apparatus as defined in claim 2, further comprising:

a second array of emitters and detectors suitable for use in absorption spectroscopy positioned substantially perpendicular to the orientation of said first array, said second array of emitters and detectors positioned so that beams emitted by said second array of emitters intersect substantially an entire cross-sectional area of said exhaust plume along a predetermined length of said exhaust plume, before said beams are received by said second array of detectors, and further intersect a substantial portion of the beams produced from said first array of emitters and detectors, said second array detecting the amount of said first pollutant so that said computer can more accurately determine the amount of said first pollutant.

12. An apparatus as defined in claim 3, further comprising:
a second array of emitters and detectors suitable for use in absorption spectroscopy positioned substantially perpendicular to the orientation of said first array, said second array of emitters and detectors positioned so that beams emitted by said second array of emitters intersect substantially an entire cross-sectional area of said exhaust plume along a predetermined length of said exhaust plume, before said beams are received by said second array of detectors, and further intersect a substantial portion of the beams produced from said first array of emitters and detectors, said second array detecting the amount of said first pollutant so that said computer can more accurately determine the amount of said first pollutant.

13. A method of determining pollutants in an exhaust plume of a motor vehicle moving along a road, comprising the steps of:
passing a first array of gas analyzer beams along a first beam path through a predetermined space across said motor vehicle path so that said exhaust plume generated by said motor vehicle passes through said predetermined space, said first array of beams being positioned such that substantially an entire cross-sectional segment of said exhaust plume is intersected by said first array of beams along a predetermined length of said exhaust plume;
measured the ambient amount of a first pollutant contained in said predetermined volume of space in a first measurement, and measuring the amount of said first pollutant in said predetermined volume after a motor vehicle exhaust has passed through said first array in a second measurement, said first and second measurements being performed by the use of said first array of beams;
passing a second, multi-spectral gas analyzer beam along a second beam path adjacent said motor vehicle, said second beam path having sufficient length to allow a determination of the change in concentration of a plurality of pollutants from said exhaust plume intersecting beam second path relative to the concentration of said plurality of pollutants before said motor vehicle began to traverse said road, said plurality of pollutants including said first pollutant;
measuring the ambient concentration of said plurality of pollutants in said exhaust plume intersecting said beam path of said second gas analyzer beam in a third measurement, said third measurement including the concentration of said first pollutant, and in a fourth measurement - measuring the concentration of said plurality of pollutants after said motor vehicle exhaust has passed through said second beam, said third and fourth measurements using said second gas analyzer beam;
calculating a ratio by determining the relative increase in the amount of said first pollutant in the predetermined volume by use of said first and second measurements, and dividing that relative increase by the relative increase in the concentration of said first pollutant as determined from said third and fourth measurements;
determining the relative increase in the amount per unit volume of said plurality of pollutants other than said first pollutant by using said ratio and said third and fourth concentration measurements for said plurality of gases.

14. A method as defined in claim 13, wherein the weight of pollutants per unit volume is determined for said plurality of pollutants.

15. A method as defined in claim 13, further comprising the step of:
measuring the velocity of said motor vehicle as it passes said predetermined space of said first array, and using said velocity to determine the amount of said pollutants per unit of distance traveled.

16. A method as defined in claim 13, further comprising the step of:
temporarily enclosing said exhaust from said motor vehicle in a tunnel during said second and fourth measurements.

17. A method as defined in claim 16, further comprising the steps of:
passing a second array of gas analyzer beams along a second beam path through a predetermined space across said motor vehicle path so that said exhaust plume generated by said motor vehicle passes through said predetermined space, said second array of beams being positioned such that substantially an entire cross-sectional segment of said exhaust plume is intersected by said second array of beams along a predetermined length of said exhaust plume, said second array of beams being at an angle to, and intersecting a substantial portion of, said first array of beams; and
using said second array of beams to take additional measurements concerning the relative change in the amount of said first pollutant contained in said predetermined volume of space before said motor vehicle began to traverse said road, and after said motor vehicle began to traverse said road, and using said additional measurements to determine the amount of pollutants per unit volume for said plurality of pollutants.

18. A method as defined in claim 16, further comprising the steps of:
enclosing said exhaust plume intersected by said first and second arrays and intersected by said second gas analyzer beam, to inhibit environmental disturbance of said exhaust plume.

19. A method as defined in claim 13, further comprising the step of:
temporarily enclosing said exhaust from said motor vehicle in a tunnel during said measuring steps.

20. A method of determining pollutants in an exhaust plume of a motor vehicle moving along a road, comprising the steps of:
passing a first array of gas analyzer beams along a first beam path through a predetermined space across said motor vehicle path so that said exhaust plume generated by said motor vehicle passes through said predetermined space, said first array of beams being positioned such that substantially an entire cross-sectional segment of said exhaust plume is intersected by said first array of beams;
measuring the increase in the amount of a first pollutant contained in a predetermined volume of space relative to the amount of said first pollutant after a motor vehicle exhaust has passed through said first array, using said first array of beams and further measuring the percentage increase of said first pollutant;

passing a second, multi-spectral gas analyzer beam along a second beam path adjacent said motor vehicle, said second beam path having sufficient length to allow a determination of the change in concentration of a plurality of pollutants in said exhaust plume along said beam path relative to the concentration before said motor vehicle began to traverse said road, said plurality of pollutants including said first pollutant;

measuring the change in concentration of said plurality of pollutants of said exhaust plume which intersect said beam path of said second gas analyzer beam, relative to the concentration when said motor vehicle began to traverse said road, using said second gas analyzer beam;

determining the ratio of the relative increase determined from said first array, to the relative increase of said first pollutant from said second beam, and using that ratio with the relative change in concentration of said plurality of gases from said second gas analyzer beam to determine the relative increase in the amount per unit volume of said plurality of pollutants other than said first pollutant.

21. The method as defined in claim 20, comprising the further step of:

measuring the velocity of said motor vehicle as it passes said predetermined space of said first array, and using said velocity to determine the amount of said pollutants per unit of distance traveled.

* * * * *